United States Patent
Matsuura et al.

(10) Patent No.: US 9,085,503 B2
(45) Date of Patent: Jul. 21, 2015

(54) METHOD FOR PRODUCING 1,3-DIMETHYLADAMANTANE

(75) Inventors: Yutaka Matsuura, Kurashiki (JP); Mitsuharu Kitamura, Kurashiki (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 13/884,378

(22) PCT Filed: Nov. 8, 2011

(86) PCT No.: PCT/JP2011/075694
§ 371 (c)(1),
(2), (4) Date: May 9, 2013

(87) PCT Pub. No.: WO2012/063809
PCT Pub. Date: May 18, 2012

(65) Prior Publication Data
US 2013/0225889 A1 Aug. 29, 2013

(30) Foreign Application Priority Data
Nov. 12, 2010 (JP) ................................. 2010-254189

(51) Int. Cl.
*C07C 13/28* (2006.01)
*C07C 5/31* (2006.01)
*C07C 5/29* (2006.01)

(52) U.S. Cl.
CPC ... *C07C 5/31* (2013.01); *C07C 5/29* (2013.01); *C07C 2103/20* (2013.01); *C07C 2103/74* (2013.01); *C07C 2527/1206* (2013.01); *C07C 2527/1213* (2013.01)

(58) Field of Classification Search
None
See application file for complete search history.

(56) References Cited

U.S. PATENT DOCUMENTS

| 3,128,316 | A | | 4/1964 | Schneider |
| 3,275,700 | A | * | 9/1966 | Janoski et al. ................ 585/352 |
| 3,641,167 | A | * | 2/1972 | Moore et al. ................. 570/130 |
| 3,944,626 | A | | 3/1976 | Honna et al. |
| 4,783,565 | A | | 11/1988 | Naruse et al. |
| 6,472,575 | B2 | | 10/2002 | Kawai et al. |
| 8,188,326 | B2 | | 5/2012 | Kawai et al. |
| 2001/0051755 | A1 | | 12/2001 | Kawai et al. |
| 2011/0112346 | A1 | * | 5/2011 | Kawai et al. ................ 585/317 |

FOREIGN PATENT DOCUMENTS

| JP | 41-11613 B1 | 6/1966 |
| JP | S41-11613 B1 | 6/1966 |
| JP | 50-32154 A | 3/1975 |
| JP | S52-2909 B2 | 1/1977 |
| JP | 53-28154 A | 3/1978 |
| JP | 55-38935 B1 | 10/1980 |
| JP | S62-265238 A | 11/1987 |
| JP | 63-295519 A | 12/1988 |
| JP | H04-37052 B2 | 6/1992 |
| JP | 2001-151705 A | 6/2001 |
| JP | 2001-151706 A | 6/2001 |
| JP | 2001-354598 A | 12/2001 |
| WO | 2009/139319 A1 | 11/2009 |

OTHER PUBLICATIONS

International Search Report dated Dec. 27, 2011, issued in International Application PCT/JP2011/075694.
International Preliminary Patentability Report dated Dec. 27, 2011, issued in International Application PCT/JP2011/075694.

* cited by examiner

*Primary Examiner* — Tam M Nguyen
(74) *Attorney, Agent, or Firm* — Fitch, Even, Tabin & Flannery, LLP

(57) ABSTRACT

According to the present invention, a method can be provided for producing 1,3-dimethyladamantane represented by formula (2) by performing a skeletal isomerization reaction using, as catalysts, 0.5 to 1.5 parts by weight of HF and 0.05 to 0.5 parts by weight of $BF_3$ with respect to 1 part by weight of perhydroacenaphthene represented by formula (1) under a reaction temperature of 60 to 110° C.

11 Claims, No Drawings

METHOD FOR PRODUCING 1,3-DIMETHYLADAMANTANE

CROSS-REFERENCE TO RELATED APPLICATIONS

This Application is a U.S. National Stage Application filed under 35 U.S.C. §371 of International Application PCT/JP2011/075694, filed Nov. 8, 2011, designating the United States, which claims priority from Japanese Patent Application 2010-254189, filed Nov. 12, 2010, the complete disclosures of which are hereby incorporated herein by reference in their entirety for all purposes.

TECHNICAL FIELD

The present invention relates to a method for producing 1,3-dimethyladamantane represented by the following formula (2) industrially advantageously from perhydroacenaphthene represented by the following formula (1) by use of $HF·BF_3$ catalysts.

[Chemical formula 1]

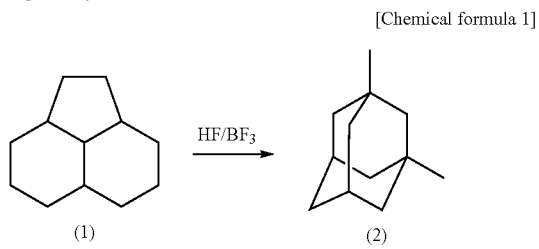

BACKGROUND ART 1,3-dimethyladamantane is expected to be useful as a material of various types of fine chemicals including pharmaceutical drugs, and a dicarboxylic acid and a diol thereof are expected to be useful as a highly functional polymer material.

Conventionally, Patent Document 1 describes hydrogenating acenaphthene represented by the following formula (3) to obtain perhydroacenaphthene (hereinafter, may be referred to simply as "PHA") represented by the following formula (1) including four types of stereoisomers.

[Chemical formula 2]

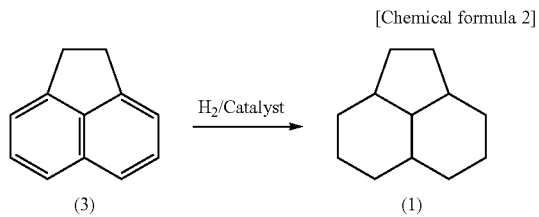 [SMILES: c1cc2c3c(cccc3c1)CC2 ; C1CC2CCCC3CCC(C1)C23]

According to Patent Document 2, a method for obtaining 1,3-dimethyladamantane from PHA using a zeolite catalyst which is ion-exchanged with Ca and La and is containing Pt and Re, under the presence of $H_2$ and HCl is known. However, the method of obtaining 1,3-dimethyladamantane from PHA has problems that the yield is as low as 38.7% and that Pt and Re in the catalyst are costly.

For producing adamantane with no substituent, a technology of using tetrahydrodicyclopentandiene as a material and using $HF·BF_3$ as catalysts is known (see, for example, Patent Documents 3 and 4). However, no method of selectively producing 1,3-dimethyladamantane at a high yield by use of $HF·BF_3$ catalysts is known so far.

For producing 1,3-dimethyladamantane by use of an acidic catalyst, a method of using aluminum chloride is known. However, in order to obtain 1,3-dimethyladamantane at a high yield, it is indispensable to use 1,2-dichloroethane, which is costly, as a catalyst component. In addition, aluminum chloride is not reusable and thus a large amount of waste derived from aluminum chloride is generated. For these reasons, the method of using aluminum chloride is not industrially advantageous (Patent Document 5).

CITATION LIST

Patent Literature

Patent Document 1: Japanese Laid-Open Patent Publication No. Sho-62-265238
Patent Document 2: Japanese Patent Publication for Opposition No. Sho-52-2909
Patent Document 3: Japanese Patent Publication for Opposition No. Sho-55-38935
Patent Document 4: Japanese Laid-Open Patent Publication No. 2001-151705
Patent Document 5: Japanese Patent Publication for Opposition No. Hei-4-37052

SUMMARY OF INVENTION

Technical Problem

A problem to be solved by the present invention is to provide a method for producing 1,3-dimethyladamantane at a high yield, which solves the above-described problems of the conventional art, does not need a costly catalyst, and allows a catalyst used to be recovered.

Solution To Problem

The present inventors, as a result of accumulating active studies on an isomerization reaction of obtaining 1,3-dimethyladamantane from perhydroacenaphthene as a material, found an industrially advantageous method capable of producing 1,3-dimethyladamantane at a high yield, by which $HF·BF_3$ catalysts are effective and recoverable by limited reaction conditions and no solvent is necessary, and thus reached the present invention.

Namely, the present invention is directed to the following.
<1> A method for producing 1,3-dimethyladamantane represented by the following formula (2) by performing a skeletal isomerization reaction using, as catalysts, 0.5 to 1.5 parts by weight of HF and 0.05 to 0.5 parts by weight of $BF_3$ with respect to 1 part by weight of perhydroacenaphthene represented by the following formula (1) under a reaction temperature of 60 to 110° C.:

[Chemical formula 3]

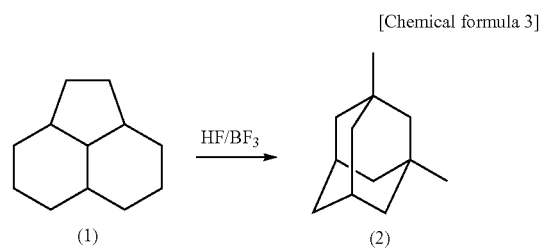

<2> The method for producing 1,3-dimethyladamantane according to <1>, wherein HF and $BF_3$ recovered from a reaction product solution are reused for the reaction.

<3> The method for producing 1,3-dimethyladamantane according to <1> or <2>, wherein a catalyst layer separated from the reaction product solution by liquid-liquid separation is supplied to a distillation tower in which at least one selected from the group consisting of benzene, toluene, hexane and heptane is circulated, thereby recovering $BF_3$ and HF and using $BF_3$ and HF for the reaction.

<4> The method for producing 1,3-dimethyladamantane according to any one of <1> through <3>, wherein the reaction temperature is 60 to 90° C.

<5> The method for producing 1,3-dimethyladamantane according to any one of <1> through <3>, wherein the reaction temperature is 80 to 105° C.

Advantageous Effects of Invention

According to a method of the present invention, no solvent is used. Therefore, a step of removing a solvent and a denatured substance thereof is not necessary. In addition, no costly catalyst is required, and a catalyst used can be recovered. Thus, 1,3-dimethyladamantane can be produced at a high yield and advantageously in terms of cost while environmental load is reduced.

DESCRIPTION OF EMBODIMENTS

Hereinafter, the present invention will be described in detail. A production method according to the present invention is a method for producing 1,3-dimethyladamantane from perhydroacenaphthene as a material by use of $HF \cdot BF_3$ as catalysts while no solvent is used. In this specification, "$HF \cdot BF_3$" indicates a state where HF and $BF_3$ coexist in a reaction system, and may be represented as $HF$-$BF_3$, $HF/BF_3$ or $HF:BF_3$. George A. Olah is a leading researcher on strong acids, and a book by George A. Olah et al., "SUPERACIDS", describes on page 51 that $HF \cdot BF_3$ in a reaction system is in the following equilibrium state.

  [Chemical formula 4]

There are four types of stereoisomers of PHA. The isomers are used as a material independently or in a mixed state. PHA can be prepared by a known method described in the Background Art.

HF, which is a catalyst, is used in an amount in the range of 0.5 to 1.5 parts by weight, preferably in an amount in the range of 0.5 to 0.7 parts by weight, with respect to 1 part by weight of PHA as the material. When HF is used in an amount less than 0.5 parts by weight, the yield of 1,3-dimethyladamantane is decreased. When HF is used in an amount more than 1.5 parts by weight, 1,3-dimethyladamantane is obtained at a high yield; but when the amount of HF is excessively large, a load is imposed on separation and recovery of HF, which is not industrially practical.

$BF_3$ is used in an amount in the range of 0.05 to 0.5 parts by weight, preferably in an amount in the range of 0.1 to 0.2 parts by weight, with respect to 1 part by weight of PHA as a material. When $BF_3$ is used in an amount less than 0.05 parts by weight, an isomerization reaction does not proceed sufficiently, and thus the selectivity and yield of 1,3-dimethyladamantane are decreased. When $BF_3$ is used in an amount more than 0.5 parts by weight, the yield of adamantane is increased, but a large amount of high boiling point compound is generated. In consideration of the load on a separation and purification step, use of such an amount of $BF_3$ is not industrially practical. In addition, the reaction pressure is too high, which is industrially problematic.

The substantial yield of 1,3-dimethyladamantane can be increased by recovering and reusing 1-ethyladamantane, which is a reaction intermediate.

For the skeletal isomerization reaction according to the present invention, no solvent is needed.

A preferable reaction temperature is 60° C. or higher, 70° C. or higher, or 80° C. or higher. A preferable reaction temperature is 110° C. or lower, 105° C. or lower or 90° C. or lower. For example, a temperature in the range of 60° C. to 110° C., in the range of 60° C. to 90° C., in the range of 80° C. to 105° C. or the like is preferable. A preferable range of reaction temperature is not limited to a combination of such temperature ranges. When the reaction temperature is lower than 60° C., the reaction is extremely slow. When the reaction temperature is higher than 110° C., the reaction rate is high, but it is difficult to control the reaction and the amount of high boiling point compound is increased. Therefore, the yield and selectivity are decreased, which is not preferable.

The reaction time, which varies in accordance with the amount of PHA or the reaction temperature, is 2 to 10 hours.

It is preferable that there are facilities for re-supplying unreacted 1-ethyladamantane obtained in the separation and purification step to a reaction tank. When the reaction product is left still after the reaction, two layers, namely, an organic layer containing adamantane and a catalyst layer containing a high boiling point compound generated as a by-product are separated from each other. Therefore, it is preferable that there are facilities for liquid-liquid separation. Alternatively, a catalyst recovery step may be used also for performing the liquid-liquid separation. In this specification, the "catalyst recovery step" is a step of recovering HF and $BF_3$ from a reaction solution obtained after the isomerization reaction. The catalyst recovery step is carried out as follows. The total amount of reaction solution or the catalyst layer is supplied to a distillation tower in which hydrocarbon is circulated. As a result, HF having a boiling point of 20° C. is recovered as a liquid from a condenser in a top part of the tower, and $BF_3$, which has a boiling point of $-100°$ C. and thus is not liquefied in the condenser in the top part of the tower, is recovered as a gas. A hydrocarbon solution containing 1,3-dimethyladamantane is recovered from a bottom part of the tower.

A reaction product solution is obtained as a liquid containing 1,3-dimethyladamantane, 1-ethyladamantane as a reaction intermediate, a by-product, and $HF \cdot BF_3$. When being left still, the reaction product solution is divided into two layers, namely, an organic layer containing 1,3-dimethyladamantane and a catalyst layer containing a high boiling point compound generated as a by-product. Therefore, the organic layer can be obtained by liquid-liquid separation. The separated catalyst layer is supplied to the distillation tower in which one or a plurality of types of hydrocarbon selected from the group consisting of, for example, benzene, toluene, hexane, heptane and the like are circulated. As a result, $BF_3$ can be recovered from the top part of the tower and HF can be recovered from the condenser at the top part of the tower, and $BF_3$ and HF are reusable as catalysts. The obtained organic layer is neutralized and washed with water, and then is treated with a usual method of distillation or the like for purification. As a result, 1,3-dimethyladamantane can be obtained.

Alternatively, the reaction product solution may not be left still and thus may not be divided into two phases, namely, the organic layer containing 1,3-dimethyladamantane and the catalyst layer containing a high boiling point compound generated as a by-product. All the amount of reaction product solution may be supplied to the above-described distillation tower in which hydrocarbon is circulated. In this case also, $BF_3$ can be recovered from the top part of the tower and HF can be recovered from the condenser in the top part of the tower, and $BF_3$ and HF can be reused as catalysts. A hydrocarbon solution containing 1,3-dimethyladamantane can be recovered from the bottom part of the tower. The amount of hydrocarbon used in this process is 1.5 to 3 parts by weight with respect to 1 part by weight of 1,3-dimethyladamantane generated.

The obtained hydrocarbon solution containing 1,3-dimethyladamantane is neutralized and washed with water, and then is treated with a usual method of distillation or the like for purification. Thus, 1,3-dimethyladamantane can be obtained.

EXAMPLES

Now, the present invention will be described specifically by way of examples. The present invention is not limited to the following examples. The reaction products were analyzed by a gas chromatography device (GC device) under the following conditions.

Device: GC-17A (produced by Shimadzu Corporation)
Used column: HR-1 (produced by Shinwa Chemical Industries, Ltd.)
Analysis conditions: Injection Temp. 310° C.; Detector Temp. 310° C.
Column temperature: kept at 100° C. for 0 minute, then increased to 300° C. at 5° C./min., then kept at 300° C. for 5 minutes
Detector: Flame ionization detector (FID)
Method: The reaction product solution is extracted into a polypropylene receiver containing distilled water. The amount of distilled water may be any amount which is sufficient for HF prepared for the reaction. The reaction product solution is left still to obtain an organic layer by liquid-liquid separation. The organic layer is once washed with a 2% aqueous solution of sodium hydroxide (sodium hydroxide: produced by Wako Pure Chemical Industries, Ltd.; water: distilled water), and is once washed with distilled water. To 0.2 g of the obtained organic layer, 0.1 g of dibenzyl, which is as an internal standard substance (produced by Wako Pure Chemical Industries, Ltd.) is added. The resultant substance is diluted with heptane, and then is put into the gel chromatography device.

Example 1

PHA was subjected to an isomerization reaction by use of a Hastelloy autoclave having a capacity of 0.5 L and including an electromagnetic stirring device, a heating device, a gas and liquid supply opening and a reaction product discharge opening. 50 g (2.5 mol) of HF produced by Morita Chemical Industries Co., Ltd. and 100 g (0.6 mol) of PHA were put to a reactor, and 16 g (0.24 mol) of $BF_3$ produced by Stella Chemifa Corporation was supplied. Then, these substances were heated to a temperature of 100° C. by the heating device with no solvent, and stirred for 4 hours while the temperature was kept at 100° C. The reaction product solution was sampled. The yield of 1,3-dimethyladamantane was 77% with respect to PHA as the material. The yield of 1-ethyladamantane as an intermediate was 15% with respect to PHA as the material, while no high boiling point compound was observed. Then, as a result of being left still, the reaction product solution was divided into two layers, namely, an organic layer containing 1,3-dimethyladamantane and a catalyst layer. The catalyst layer was obtained by liquid-liquid separation. The separated catalyst layer was supplied to a distillation tower in which heptane was circulated. As a result, almost all the amount of $BF_3$ was recovered from a top part of the tower, and almost all the amount of HF was recovered from a condenser in the top part of the tower.

Example 2

A reaction was carried out under substantially the same conditions as those in Example 1 except that HF and $BF_3$ recovered in Example 1 were used. The yield of 1,3-dimethyladamantane was 75%, and deactivation of the catalysts was not observed. Like in Example 1, no high boiling point compound was observed.

Example 3

PHA was subjected to an isomerization reaction by use of a Hastelloy autoclave having a capacity of 0.5 L and including an electromagnetic stirring device, a heating device, a gas and liquid supply opening and a reaction product discharge opening. 50 g (2.5 mol) of HF produced by Morita Chemical Industries Co., Ltd. and 100 g (0.6 mol) of PHA were put to a reactor, and 16 g (0.24 mol) of $BF_3$ produced by Stella Chemifa Corpration was supplied. Then, these substances were heated to a temperature of 80° C. by the heating device with no solvent, and stirred for 4 hours while the temperature was kept at 80° C. The reaction product solution was sampled. The yield of 1,3-dimethyladamantane was 51% with respect to PHA as the material. The yield of 1-ethyladamantane as an intermediate was 42% with respect to PHA as the material, while no high boiling point compound was observed. Then, as a result of being left still, the reaction product solution was divided into two layers, namely, an organic layer containing 1,3-dimethyladamantane and a catalyst layer. The catalyst layer was obtained by liquid-liquid separation. The separated catalyst layer was supplied to a distillation tower in which heptane was circulated. As a result, almost all the amount of $BF_3$ was recovered from a top part of the tower, and almost all the amount of HF was recovered from a condenser in the top part of the tower.

Example 4

A reaction was carried out under substantially the same conditions as those in Example 3 except that HF and $BF_3$ recovered in Example 3 were used. The yield of 1,3-dimethyladamantane was 51%, and deactivation of the catalysts was not observed. Like in Example 3, no high boiling point compound was observed.

Comparative Example 1

A reaction was carried out under substantially the same conditions as those in
Example 1 except that the reaction temperature was 50° C. The yield of 1,3-dimethyladamantane was merely 32%.

Comparative Example 2

A reaction was carried out under substantially the same conditions as those in Example 1 except that the reaction temperature was 130° C. The yield of 1,3-dimethyladamantane was 63%, but 15% of high boiling point compound was generated, which was not preferable.
Industrial Applicability [0027]
According to the present invention, no solvent is used. Therefore, a step of removing a solvent and a denatured substance thereof is not necessary. In addition, no costly catalyst is required, and a catalyst used can be recovered and reused. 1,3-dimethyladamantane can be produced at a high yield and advantageously in terms of cost while environmental load is reduced.

The invention claimed is:

1. A method for producing 1,3-dimethyladamantane represented by the following formula (2) by performing a skeletal isomerization reaction using, as catalysts, 0.5 to 1.5 parts by weight of HF and 0.1 to 0.5 parts by weight of $BF_3$ with respect to 1 part by weight of perhydroacenaphthene represented by the following formula (1) under a reaction temperature of 60 to 110° C.:

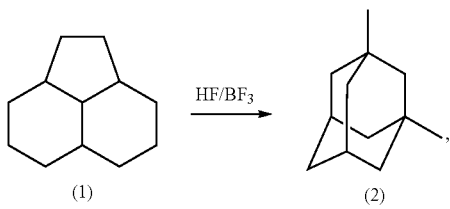

wherein the yield of 1,3-dimethyladamantane is higher than that of 1-ethyladamantane which is a reaction intermediate.

2. The method for producing 1,3-dimethyladamantane according to claim 1, wherein HF and $BF_3$ recovered from a reaction product solution are reused for the reaction.

3. The method for producing 1,3-dimethyladamantane according to claim 1, wherein a catalyst layer separated from the reaction product solution by liquid-liquid separation is supplied to a distillation tower in which at least one selected from the group consisting of benzene, toluene, hexane and heptane is circulated, thereby recovering $BF_3$ and HF and using $BF_3$ and HF for the reaction.

4. The method for producing 1,3-dimethyladamantane according to claim 1, wherein the reaction temperature is 60 to 90° C.

5. The method for producing 1,3-dimethyladamantane according to claim 1, wherein the reaction temperature is 80 to 105° C.

6. The method for producing 1,3-dimethyladamantane according to claim 2, wherein a catalyst layer separated from the reaction product solution by liquid-liquid separation is supplied to a distillation tower in which at least one selected from the group consisting of benzene, toluene, hexane and heptane is circulated, thereby recovering $BF_3$ and HF and using $BF_3$ and HF for the reaction.

7. The method for producing 1,3-dimethyladamantane according to claim 6, wherein the reaction temperature is 60 to 90° C.

8. The method for producing 1,3-dimethyladamantane according to claim 7, wherein the reaction temperature is 80 to 105° C.

9. A method for producing 1,3-dimethyladamantane represented by the following formula (2) by performing a skeletal isomerization reaction using, as catalysts, 0.5 to 1.5 parts by weight of HF and 0.05 to 0.5 parts by weight of $BF_3$ with respect to 1 part by weight of perhydroacenaphthene represented by the following formula (1) under a reaction temperature of 60 to 110° C.:

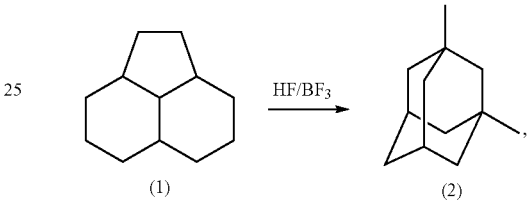

wherein the yield of 1,3-dimethyladamantane is from 51% to 77% with respect to perhydroacenaphthene.

10. The method for producing 1,3-dimethyladamantane according to claim 1, wherein 0.5 to 0.7 parts by weight of HF with respect to 1 part by weight of perhydroacenaphthene is used.

11. The method for producing 1,3-dimethyladamantane according to claim 1, wherein 0.1 to 0.2 parts by weight of $BF_3$ with respect to 1 part by weight of perhydroacenaphthene is used.

* * * * *